US008519342B2

(12) United States Patent
Yamada et al.

(10) Patent No.: US 8,519,342 B2
(45) Date of Patent: Aug. 27, 2013

(54) NUCLEAR MEDICINE IMAGING APPARATUS, CONTROL METHOD, AND COMPUTER PROGRAM PRODUCT

(75) Inventors: Yasunobu Yamada, Nasushiobara (JP); Takuzo Takayama, Utsunomiya (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 187 days.

(21) Appl. No.: 13/153,028

(22) Filed: Jun. 3, 2011

(65) Prior Publication Data

US 2011/0297835 A1 Dec. 8, 2011

(30) Foreign Application Priority Data

Jun. 4, 2010 (JP) ................................ 2010-128936

(51) Int. Cl.
*G01T 1/166* (2006.01)
(52) U.S. Cl.
USPC ............................... 250/363.04; 250/363.02
(58) Field of Classification Search
USPC ............. 250/363.01, 363.02, 363.03, 363.04, 250/363.05, 367, 370.09, 370.11
See application file for complete search history.

(56) References Cited

U.S. PATENT DOCUMENTS

2008/0103391 A1* 5/2008 Dos Santos Varela ........ 600/436
2009/0112530 A1* 4/2009 Vija et al. .......................... 703/2

FOREIGN PATENT DOCUMENTS

CN 101213475 A 7/2008
JP 2007-107995 4/2007

OTHER PUBLICATIONS

Chinese Office Action issued May 10, 2013, in Chinese Patent Application No. 201110154951.0.

* cited by examiner

*Primary Examiner* — Mark R Gaworecki
(74) *Attorney, Agent, or Firm* — Oblon, Spivak, McClelland, Maier & Neustadt, L.L.P.

(57) ABSTRACT

A nuclear medicine imaging apparatus according to an embodiment of the invention includes a detector, a measuring unit, and an end control unit. The detector is configured to detect radiation for generating a nuclear medicine image. The measuring unit is configured to measure the number of times the detector detects the radiation. The end control unit is configured to control the detector to end the detection operation when the number of times measured by the measuring unit is equal to or less than a threshold value.

10 Claims, 8 Drawing Sheets

FIG.7

| MODULE ID | SCINTILLATOR NUMBER | ENERGY VALUE | DETECTION TIME |
|---|---|---|---|
| D1 | P11 | E11 | T11 |
| | P12 | E12 | T12 |
| | P13 | E13 | T13 |
| | ⋮ | ⋮ | ⋮ |
| D2 | P21 | E21 | T21 |
| | P22 | E22 | T22 |
| | P23 | E23 | T23 |
| | ⋮ | ⋮ | ⋮ |
| D3 | P31 | E31 | T31 |
| | P32 | E32 | T32 |
| | P33 | E33 | T33 |
| | ⋮ | ⋮ | ⋮ |
| ⋮ | ⋮ | ⋮ | ⋮ |

| COUNT INFORMATION A | | | COUNT INFORMATION B | | |
|---|---|---|---|---|---|
| SCINTILLATOR NUMBER | ENERGY VALUE | DETECTION TIME | SCINTILLATOR NUMBER | ENERGY VALUE | DETECTION TIME |
| P11 | E11 | T11 | P22 | E22 | T22 |
| P12 | E12 | T12 | P32 | E32 | T32 |
| P13 | E13 | T13 | P33 | E33 | T33 |
| ⋮ | ⋮ | ⋮ | ⋮ | ⋮ | ⋮ |

NUCLEAR MEDICINE IMAGING APPARATUS, CONTROL METHOD, AND COMPUTER PROGRAM PRODUCT

CROSS-REFERENCE TO RELATED APPLICATION(S)

This application is based upon and claims the benefit of priority from Japanese Patent Application No. 2010-128936, filed on Jun. 4, 2010; the entire contents of which are incorporated herein by reference.

FIELD

Embodiments described herein relate generally to a nuclear medicine imaging apparatus, a control method, and a computer program product.

BACKGROUND

Conventionally, nuclear medicine imaging apparatuses, such as a gamma camera, a single photon emission computed tomography (SPECT) apparatus, and a positron emission tomography (PET) apparatus, have been known. The nuclear medicine imaging apparatus includes a detector that detects radiation. The nuclear medicine imaging apparatus detects radiation emitted from an isotope or a labeled compound which is introduced into body tissues using the detector and forms the image of the dose distribution of the radiation detected by the detector, thereby reconstructing a nuclear medicine image that provides the functional information of the body tissues.

For example, a radioactive drug including a labeled compound that is frequently introduced into tumor tissues is put into the body of the examinee. Then, the nuclear medicine imaging apparatus detects radiation emitted from the labeled compound for a predetermined period of time and reconstructs a nuclear medicine image including the distribution of the tumor tissues of the examinee into which the labeled compound is introduced.

In addition, in recent years, apparatuses have been proposed in which a nuclear medicine imaging apparatus that provides functional information is integrated with an X-ray computed tomography (X-ray CT) apparatus that provides shape information. For example, the following apparatuses have been proposed: a PET-CT apparatus in which a PET apparatus and an X-ray CT apparatus are integrated with each other; and a SPECT-CT apparatus in which a SPECT apparatus and an X-ray CT apparatus are integrated with each other.

However, in the related art, in some cases, measurement is continuously performed in a state in which radiation may not be detected. In general, the half-life of the isotope or the labeled compound used to capture images in the nuclear medicine imaging apparatus is short. As a result, in some cases, radiation may not be detected before the nuclear medicine imaging apparatus ends its measuring operation. In this case, the nuclear medicine imaging apparatus continuously perform measurement until a predetermined period of time ends in the state in which radiation may not be detected.

BRIEF DESCRIPTION OF THE DRAWINGS

FIG. 7 is a diagram illustrating an example of count information stored in a count information table according to the first embodiment;

DETAILED DESCRIPTION

According to one embodiment, a nuclear medicine imaging apparatus includes a detector and a measuring unit and an end control unit. The detector is configured to detect radiation for generating a nuclear medicine image. The measuring unit is configured to measure the number of times the detector detects the radiation. The end control unit is configured to control the detector to end the detection operation when the number of times measured by the measuring unit is equal to or less than a threshold value.

Hereinafter, as an example of a nuclear medicine imaging apparatus, a PET-CT apparatus will be described, but the embodiment is not limited thereto. For example, any nuclear medicine imaging apparatus, such as a SPECT-CT apparatus, a PET apparatus, or a SPECT apparatus, may be used.

Figure 1:
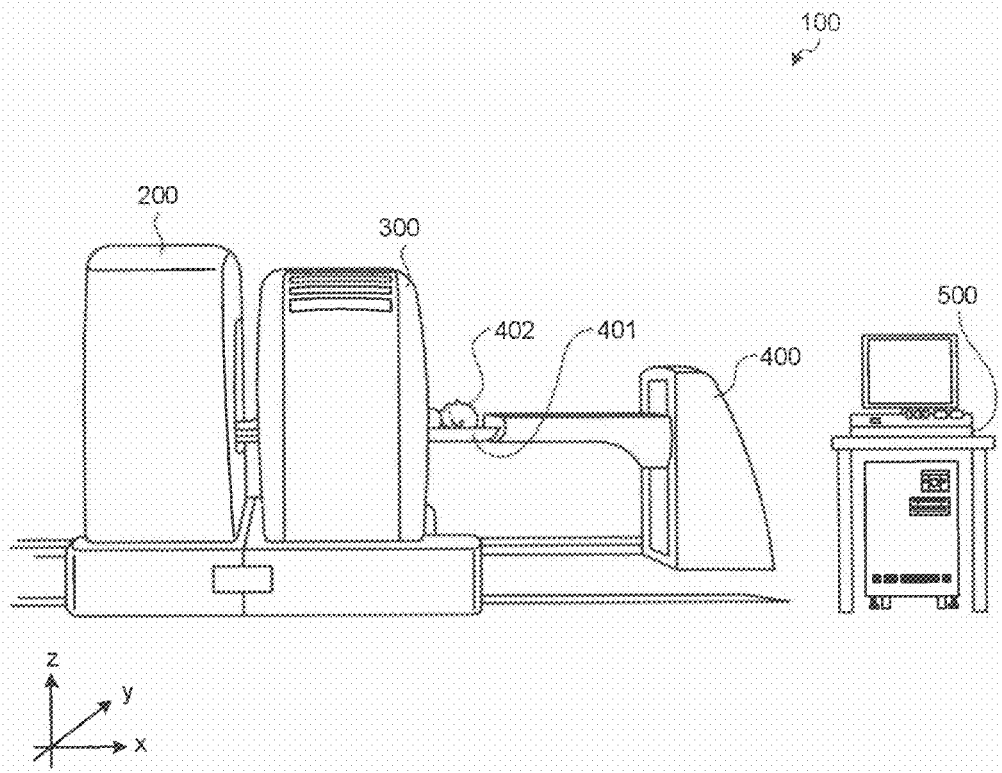
FIG. 1 is a diagram illustrating the overall structure of a PET-CT apparatus according to a first embodiment.

FIG. 1 is a diagram illustrating the overall structure of a PET-CT apparatus according to a first embodiment. In FIG. 1, reference numeral 100 indicates a PET-CT apparatus, reference numeral 200 indicates a PET scanner, reference numeral 300 indicates an X-ray CT scanner, reference numeral 400 indicates a couch, reference numeral 401 indicates a top plate on which the examinee lies, and reference numeral 402 indicates the examinee. As shown in FIG. 1, the PET-CT apparatus 100 includes the PET scanner 200, the X-ray CT scanner 300, the couch 400, and a console 500. In FIG. 1, the X direction is the body axis direction of the examinee 402 who lies on the top plate 401 shown in FIG. 1. The Y direction is a direction on the horizontal plane that is orthogonal to the X direction. The Z direction is the vertical direction.

The couch 400 includes the top plate 401 on which the examinee 402 lies. Although not shown in FIG. 1, the couch 400 includes a couch control unit that moves the top plate 401. The couch control unit is controlled by the console 500 to move the examinee 402 on the top plate 401 into an imaging hole of the PET-CT apparatus 100.

The PET scanner 200 includes a plurality of detectors 210 that detects radiation for generating a nuclear medicine image. The detectors 210 are arranged in a ring shape around the body axis of the examinee 402. For example, the detectors 210 detect a pair of gamma rays emitted from a labeled compound that is put into the body tissues of the examinee 402 on the top plate 401, from the outside of the body of the examinee 402.

Specifically, whenever the detectors 210 detect the gamma rays, the PET scanner 200 collects a detection position indicating the position where the detector 210 detects the gamma rays, an energy value at the time when the gamma rays are incident on the detector 210, and the detection time when the detector 210 detects the gamma rays. The information collected by the PET scanner 200 is referred to as "count information."

Next, the relationship between the gamma ray detected by the detector 210 and a pair of gamma rays emitted from a labeled compound introduced into the body tissues of the examinee 402 will be described. The detector 210 does not always detect both a pair of gamma rays emitted from the labeled compound. For example, when a pair of gamma rays is emitted from the labeled compound, the detector 210 may detect only one of the pair of gamma rays, may detect both the pair of gamma rays, or may not detect any of the pair of gamma rays.

The labeled compound is, for example, 18F-labeled deoxyglucose that is labeled with "18F (fluorine)," which is a positron emitting nuclide. The labeled compound is given to the examinee 402 before measurement using the PET-CT apparatus 100. However, the labeled compound is not limited to the 18F labeled deoxyglucose, but any labeled compound may be used.

The X-ray CT scanner 300 includes an X-ray tube 301 that emits X-rays for generating an X-ray CT image and an X-ray detector 302 that detects the X-rays emitted by the X-ray tube 301. In the X-ray CT scanner 300, the X-ray tube 301 emits X-rays to the examinee 402 and the X-ray detector 302 detects the X-rays passing through the examinee 402. Specifically, while the X-ray CT scanner 300 is rotated about the body axis of the examinee 402, the X-ray tube 301 emits X-rays and the X-ray detector 302 detects the X-rays. That is, the X-ray CT scanner 300 emits X-rays to the examinee 402 in multiple directions while being rotated about the body axis of the examinee 402. The emitted X-rays pass through the examinee 402 and are absorbed by the examinee 402. As a result, the intensity of the X-rays is attenuated. The X-ray CT scanner 300 detects the attenuated X-rays. Data obtained by performing an amplification process or an A/D conversion process on the X-rays detected by the X-ray detector 302 is referred to as "projection data." The X-ray CT scanner 300 collects the projection data of the X-rays detected by the X-ray detector 302 and the detection position where the X-rays used to generate the projection data are detected.

Figure 2:
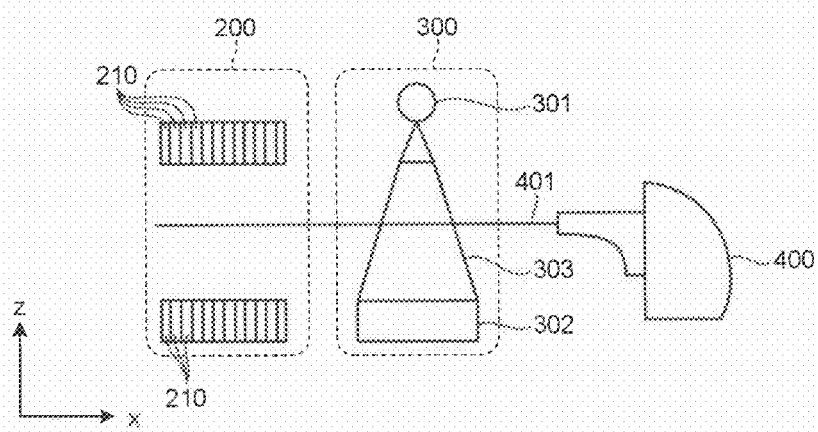
FIG. 2 is a diagram illustrating an example of the relationship between a PET scanner and an X-ray CT scanner according to the first embodiment.

FIG. 2 is a diagram illustrating an example of the relationship between the PET scanner and the X-ray CT scanner according to the first embodiment. FIG. 2 is a cross-sectional view illustrating the PET scanner 200 and the X-ray CT scanner 300, as viewed from the Y-axis direction. In FIG. 2, reference numeral 200 indicates a PET scanner, reference numeral 210 indicates a detector, reference numeral 300 indicates an X-ray CT scanner, reference numeral 301 indicates an X-ray tube, reference numeral 302 indicates an X-ray detector, and reference numeral 303 indicates an X-ray emitted by the X-ray tube 301. For convenience of explanation, FIG. 2 shows the couch 400 and the top plate 401 in addition to the PET scanner 200 and the X-ray CT scanner 300.

As shown in FIG. 2, in the PET scanner 200, a plurality of detectors 210 is arranged in the X-axis direction. The plurality of detectors 210 is arranged so as to surround the body axis of the examinee 402 in a ring shape. As shown in FIG. 2, the X-ray CT scanner 300 includes the X-ray tube 301 and the X-ray detector 302. The X-ray tube 301 and the X-ray detector 302 are arranged so as to face each other with the top plate 401, on which the examinee 402 lies during measurement, interposed therebetween.

Figure 3:
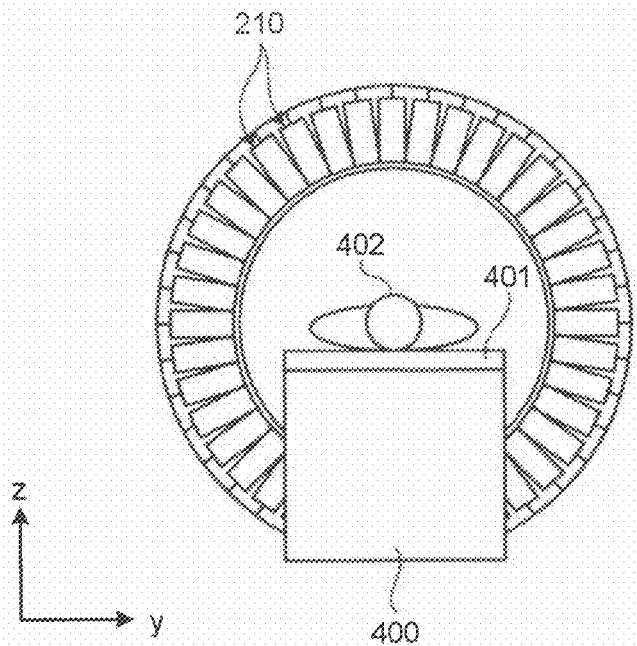
FIG. 3 is a diagram illustrating the structure of the PET scanner according to the first embodiment.

FIG. 3 is a diagram illustrating the structure of the PET scanner according to the first embodiment. In FIG. 3, reference numeral 400 indicates a couch, reference numeral 401 indicates a top plate, reference numeral 402 indicates an examinee, and reference numeral 210 indicates a detector. FIG. 3 is a cross-sectional view illustrating the PET scanner, as viewed from the X-axis direction. For convenience of explanation, FIG. 3 shows the examinee 402, the couch 400, and the top plate 401 in addition to the PET scanner 200.

As shown in FIG. 3, in the PET scanner 200, a plurality of detectors 210 is arranged so as to surround the examinee 402 in a ring shape. The detector 210 is, for example, a photon counting type.

Figure 4:
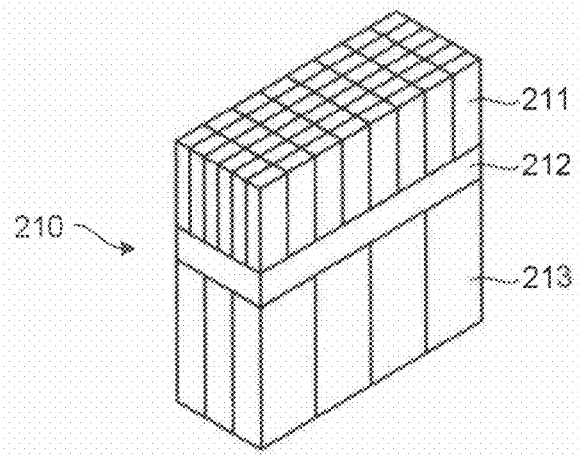
FIG. 4 is a diagram illustrating an example of the structure of a detector according to the first embodiment.

FIG. 4 is a diagram illustrating an example of the structure of the detector according to the first embodiment. In FIG. 4, reference numeral 211 indicates a scintillator, reference numeral 212 indicates a light guide, and reference numeral 213 indicates a photomultiplier tube (PMT).

As shown in FIG. 4, the detector 210 includes the scintillator 211, the light guide 212, and the photomultiplier tube 213. The scintillator 211 converts the gamma ray that is emitted from the examinee 402 and is then incident on the detector 210 into visible light and outputs the visible light. The scintillator 211 is made of, for example, NaI or BGO that converts gamma rays into visible light. As shown in FIG. 4, the scintillators 211 are two-dimensionally arranged. The visible light output by the scintillator 211 is referred to as "scintillation light." The light guide 212 transmits the visible light output from the scintillator 211 to the photomultiplier tube 213. The light guide 212 is made of, for example, a plastic material having high light transmittance. The photomultiplier tube 213 receives the visible light output by the scintillator 211 through the light guide 212 and converts the received visible light into an electric signal. A plurality of photomultiplier tubes 213 is arranged.

Next, the photomultiplier tube 213 will be described. The photomultiplier tube 213 includes a photocathode that receives the scintillation light and generates photoelectrons, a multi-stage dynode that generates an electric field for accelerating the photoelectrons generated by the photocathode, and an anode which is an outlet through which electrons flow out. The electron emitted from the photocathode by the photoelectric effect is accelerated to the dynode and collides with the surface of the dynode. As a result, a plurality of electrons is ejected from the surface of the dynode. The phenomenon in which a plurality of electrons is ejected from the surface of the dynode is repeated over the multi-stage dynode and the number of electrons increases by geometrical progression.

For example, when receiving one scintillation light component, the anode outputs about 1,000,000 electrons. The number of electrons obtained from the anode when one scintillation light component is received is referred to as "the gain of the photomultiplier tube." In this case, the gain of the photomultiplier tube 213 is "1,000,000." In addition, a voltage of 1000 V (volt) or more is generally applied between the dynode and the anode in order to increase the number of electrons in geometrical progression.

As such, in the detector 210, the scintillator 211 converts the gamma ray into scintillation light and the photomultiplier tube 213 converts the visible light into an electric signal. In this way, the detector 210 detects the gamma ray emitted from the examinee 402.

Figure 5:
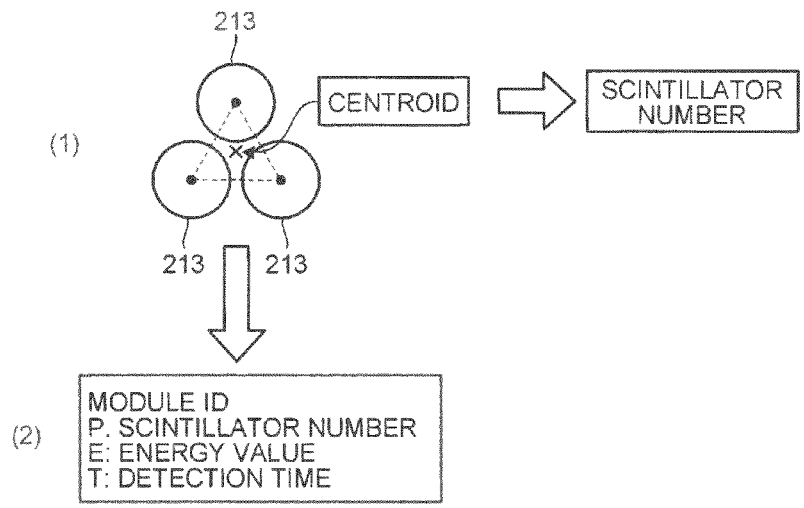
FIG. 5 is a diagram illustrating information detected by an anger-type detector according to the first embodiment.

As described above, whenever the detector 210 detects the gamma ray, the PET scanner 200 collects the detection position, the energy value, and the detection time. Next, an example of a process of calculating the detection position and the energy value when a plurality of adjacent detectors 210 detect gamma rays at the same time will be described in brief with reference to FIG. 5. FIG. 5 is a diagram illustrating information detected by an anger-type detector according to the first embodiment.

For example, the PET scanner 200 performs an anger-type position calculating process to settle the detection position. For example, when the photomultiplier tube 213 is a position-detection-type photomultiplier tube, the PET scanner 200 collects the detection position using the position-detection-type photomultiplier tube 213. As shown in (1) of FIG. 5, a case in which three photomultiplier tubes 213 convert scintillation light into electric signals and output the electric signals at the same time will be described. In this case, the PET scanner 200 acquires the position of the photomultiplier tubes 213 that output the electric signals at the same time and acquires each of the energy values of the electric signals that are output from the photomultiplier tubes 213 at the same time. Then, the PET scanner 200 calculates the centroid position from the acquired energy values and specifies the scintillator 211 corresponding to the calculated centroid position. In addition, the PET scanner 200 integrates the energy values of the electric signals output from each of the photomultiplier tubes 213 that convert the scintillation light into electric signals and output the electric signals at the same time and uses the integrated energy value as the energy value of the gamma ray incident on the detector 210.

As shown in (2) of FIG. 5, whenever the detector 210 detects the gamma ray, the PET scanner 200 collects a "scintillator number" that uniquely identifies the scintillator 211, the "energy value," and the "detection time." In the example shown in (2) of FIG. 5, in addition to the "scintillator number," the "energy value," and the "detection time," output is a "module ID" which is information uniquely identifying the detector 210.

The detection time may be absolute time, such as time, or the time elapsed from the start of the capture of a PET image. The detector 210 collects the detection time with an accuracy of, for example, 10 to 12 psec.

Next, the flow of a process when the PET-CT apparatus 100 according to the first embodiment reconstructs a PET image and an X-ray CT image will be described in brief. The PET scanner 200 and the X-ray CT scanner 300 are moved from the left to the right in FIG. 1 or FIG. 2, or the couch 400 is moved from the right to the left. The X-ray CT scanner 300 collects the projection data and then the PET scanner 200 collects the count information. Then, the console 500 reconstructs a PET image and an X-ray CT image on the basis of the collected information. However, the embodiment is not limited thereto. The PET scanner 200 and the X-ray CT scanner 300 may be moved from the right to the left in FIG. 1 or FIG. 2.

Figure 6:
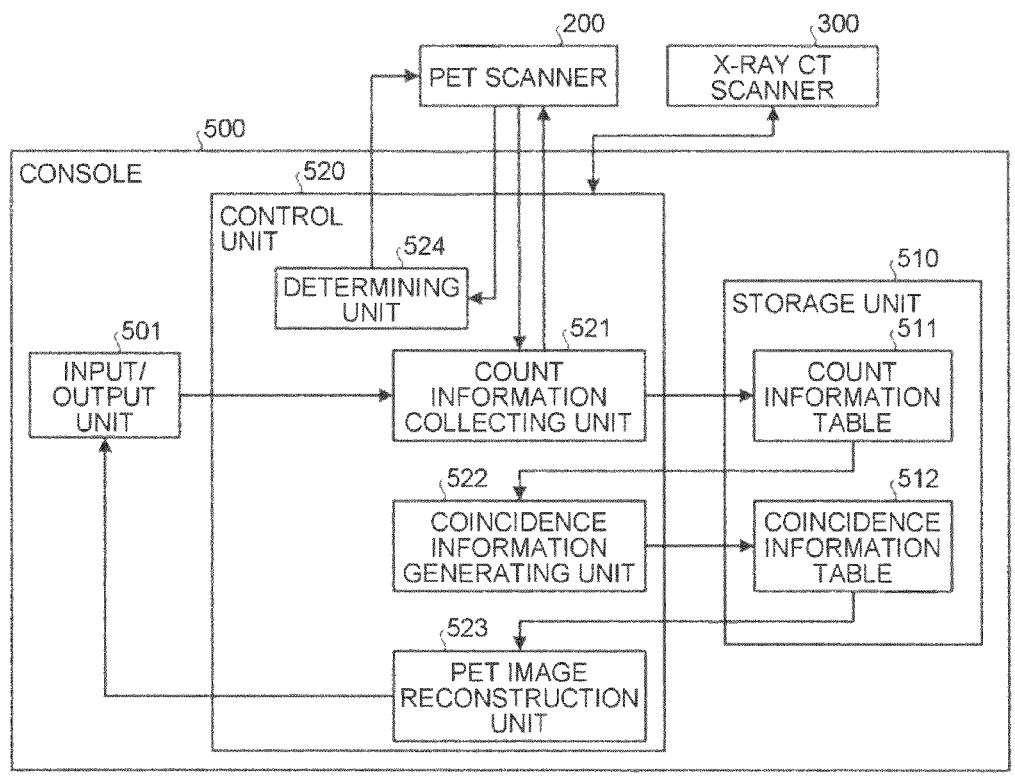
FIG. 6 is a block diagram illustrating an example of the structure of a console according to the first embodiment.

FIG. 6 is a block diagram illustrating an example of the structure of the console according to the first embodiment. The console 500 reconstructs the X-ray CT image using the information collected by the X-ray CT scanner 300. In addition, the console 500 generates coincidence information using the count information collected by the PET scanner 200 and reconstructs the PET image on the basis of the generated coincidence information. The console 500 performs a determination process and ends the detection process of the PET scanner 200 on the basis of the determination result, which will be described in detail below. A process of reconstructing the PET image or a process of reconstructing the X-ray CT image which is performed by the console 500 may be performed by any method and will be described in brief below.

For convenience of explanation, FIG. 6 shows the PET scanner 200 and the X-ray CT scanner 300 in addition to the console 500. In the example shown in FIG. 6, the console 500 includes an input/output unit 501, a storage unit 510, and a control unit 520.

The input/output unit 501 is connected to the control unit 520. The input/output unit 501 receives various kinds of instructions from the user of the PET-CT apparatus 100 and transmits the received instructions to the control unit 520. The input/output unit 501 receives information from the control unit 520 and outputs the received information to the user. For example, the input/output unit 501 is a keyboard, a mouse, a microphone, a monitor, or a speaker. A description of the details of the information or instruction received by the input/output unit 501 or the details of the information output by the input/output unit 501 will be omitted here, but the details of the information or instruction will be described below together with each unit related thereto.

The storage unit 510 is connected to the control unit 520. The storage unit 510 stores data used in various kinds of processes of the control unit 520. The storage unit 510 is, for example, a semiconductor memory device, such as a random access memory (RAM) or a flash memory, or a storage device, such as a hard disk or an optical disk. In the example shown in FIG. 6, the storage unit 510 includes a count information table 511 and a coincidence information table 512.

The count information table 511 stores the count information collected by the PET scanner 200. In the example shown in FIG. 7, the count information table 511 stores a "scintillator number," an "energy value," and a "detection time" so as to be associated with a "module ID." FIG. 7 is a diagram illustrating an example of the count information stored in the count information table according to the first embodiment.

In the example shown in FIG. 7, the count information table 511 stores a scintillator number "P11," an energy value "E11," a detection time "T11," a scintillator number "P12," an energy value "E12," and a detection time "T12" so as to be associated with a module ID "D1." That is, the count information table 511 stores that the scintillator "P11" of the detector "D1" detects a gamma ray with the energy value "E11" at the detection time "T11" and the scintillator "P12" of the detector "D1" detects a gamma ray with the energy value "E12" at the detection time "T12." In addition, the count information table 511 stores information related to the other detectors 210 in the same way as described above.

The coincidence information table 512 stores coincidence information for determining the incident direction of a pair of gamma rays which is emitted from a positron emitting nuclide. Specifically, the coincidence information table 512 stores a combination of count information items indicating a pair of gamma rays emitted from the positron emitting nuclide.

Next, the coincidence information will be described in brief. In the case in which a pair of gamma rays is emitted from the positron emitting nuclide and the detector 210 detects both the pair of gamma rays, whenever the gamma rays are emitted from the positron emitting nuclide, two count information items are collected. The coincidence information indicates a combination of two count information items collected whenever the gamma rays are emitted from the positron emitting nuclide.

Figures 8, 9:
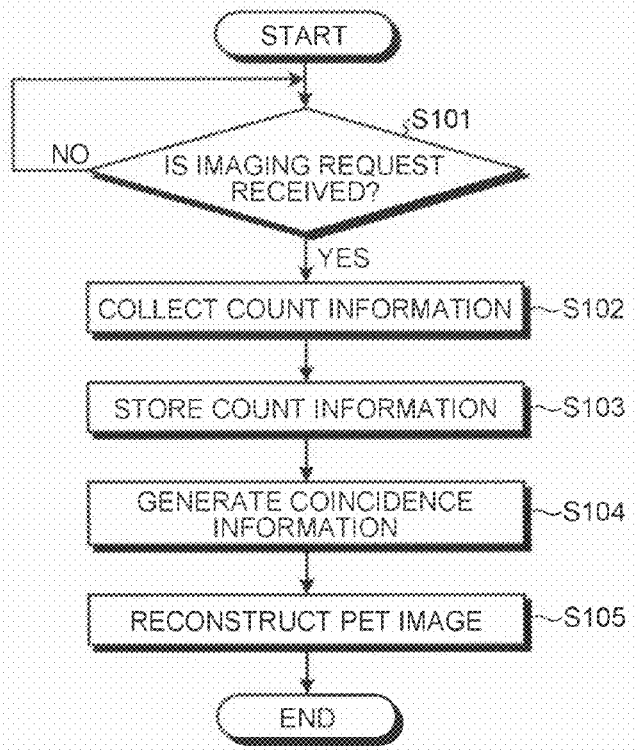
FIG. 8 is a diagram illustrating an example of coincidence information stored in a coincidence information table according to the first embodiment.
FIG. 9 is a flowchart illustrating an example of the flow of a PET image capture process of the PET-CT apparatus according to the first embodiment.

FIG. 8 is a diagram illustrating an example of the coincidence information stored in the coincidence information table according to the first embodiment. As shown in FIG. 8, the coincidence information table 512 stores a combination of two count information items. In FIG. 8, for convenience of explanation, the two count information items included in the combination of count information items are "count information A" and "count information B." In the example shown in FIG. 8, the coincidence information table 512 stores a combination of the count information A including the scintillator number "P11," the energy value "E11," and the detection time "T11" and the count information B including the scintillator number "P22," the energy value "E22," and the detection time "T22." That is, the coincidence information table 512 stores that the scintillator "P11" detects one of the pair of gamma rays emitted from the positron emitting nuclide at the detection time "T11" and the scintillator "P22" detects the other one of the pair of gamma rays emitted from the positron emitting nuclide at the detection time "T22."

The control unit 520 is connected to the input/output unit 501 and the storage unit 510. The control unit 520 includes an internal memory that stores programs for defining, for example, various kinds of procedures and controls various kinds of processes. The control unit 520 corresponds to an electronic circuit, such as an application specific integrated circuit (ASIC), a field programmable gate array (FPGA), a central processing unit (CPU), or a micro processing unit (MPU). In the example shown in FIG. 6, the control unit 520 includes a count information collecting unit 521, a coincidence information generating unit 522, a PET image reconstruction unit 523, and a determining unit 524.

When receiving an execution instruction to perform measurement from the user through the input/output unit 501, the control unit 520 operates the X-ray CT scanner 300 to receive an X-ray detection position and the projection data of the X-ray collected by the X-ray CT scanner 300. For example, the control unit 520 stores the projection data of the X-ray and the X-ray detection position in the table of the storage unit 510 (not shown in FIG. 6). Then, the control unit 520 reconstructs an X-ray CT image using the received projection data of the X-ray and the received X-ray detection position. For example, an X-ray reconstruction control unit (not shown in FIG. 6) of the control unit 520 reads the projection data of the X-ray and the X-ray detection position stored in the table (not shown in FIG. 6) of the storage unit 510 and reconstructs the X-ray CT image. The control unit 520 performs a PET dynamic imaging operation of capturing a plurality of PET images of the same part at different times.

In the control unit 520, the count information collecting unit 521, the coincidence information generating unit 522, the PET image reconstruction unit 523, and the determining unit 524 operate the PET scanner 200 to reconstruct the PET image, which will be described in detail below.

When receiving an imaging request to capture a PET image from the user through the input/output unit 501, the count information collecting unit 521 operates the PET scanner 200 to receive the count information collected by the PET scanner 200. Then, the count information collecting unit 521 stores the received count information in the count information table 511.

Whenever the PET scanner 200 collects count information, the count information collecting unit 521 receives the collected count information and stores the received count information in the count information table 511.

The coincidence information generating unit 522 searches for a combination of count information items indicating a pair of gamma rays on the basis of the energy value and detection time of the count information stored in the count information table 511 and generates coincidence information. Then, the coincidence information generating unit 522 stores the generated coincidence information in the coincidence information table 512.

Specifically, the coincidence information generating unit 522 generates the coincidence information on the basis of coincidence information generation conditions designated by the operator. The coincidence information generation conditions include a time window width and an energy window width. The time window width indicates the upper limit of the difference between two detection times when both a pair of gamma rays are received. The energy window width indicates the range of the energy value of the gamma ray.

Regardless of whether the detection times of a pair of gamma rays which is simultaneously emitted from the positron emitting nuclide are equal to or different from each other, the difference between the two detection times is very small. On the basis of this point, the coincidence information generating unit 522 uses the time window width to prevent the generation of erroneous coincidence information.

The energy values of a pair of gamma rays simultaneously emitted from the positron emitting nuclide have been known. For example, in 18F, 15O, or 11C, a radiation of "511 keV" is emitted. Therefore, the energy values of a pair of gamma rays simultaneously emitted from the positron emitting nuclide are within a predetermined range. On the basis of this point, the coincidence information generating unit 522 uses the energy window width to exclude count information, not a pair of gamma rays emitted from the positron emitting nuclide, and generates coincidence information, thereby preventing the generation of erroneous coincidence information.

For example, an example in which the coincidence information generating unit 522 generates coincidence information using a time window width of "600 psec" and an energy window width of "350 keV to 550 keV" will be described. In this case, the coincidence information generating unit 522 searches for a combination of count information items in which the difference between two detection times is within a "time window width of 600 psec" and two energy values both have an "energy window width of 350 keV to 550 keV" between modules, with reference to the "detection time (T)" and the "energy value (E)" for each "module ID".

Searching for the combination in which the detection time is within the time window width and the energy value is within a predetermined energy window width is referred to as "coincidence finding." In addition, a list of the coincidence information items generated by the coincidence information generating unit 522 is referred to as a "coincidence list."

The example in which the time window width and the energy window width are used has been described above, but the embodiment is not limited thereto. For example, the coincidence information generating unit 522 may use random correction for excluding accidental coincidence, scattering correction for excluding that the count information of a scattered gamma ray is generated as the coincidence information, sensitivity correction for correcting a difference in sensitivity between the detectors 210, and attenuation correction for correcting the energy value of the gamma ray attenuated in the examinee 402, in addition to the energy window width and the time window width.

The PET image reconstruction unit 523 reads the coincidence information stored in the coincidence information table 512 and performs a back projection process on the read coincidence information, thereby reconstructing a PET image. In addition, the PET image reconstruction unit 523 outputs the reconstructed PET image to the user through the input/output unit 501 or stores the PET image in the storage unit 510. Whenever a predetermined period of time elapses, the PET image reconstruction unit 523 reconstructs a PET image using the coincidence information generated during the predetermined period of time.

When the PET scanner 200 starts a detection process, the determining unit 524 measures the number of times the detector 210 detects radiation. In other words, the determining unit 524 calculates a count rate (count/sec). For example, the determining unit 524 measures the number of times the PET scanner 200 detects a gamma ray for one second. A case in which, whenever collecting count information, the PET scanner 200 transmits the count information to the console 500 will be described. In this case, the determining unit 524 measures the number of times the count information is received from the PET scanner 200 for one second. The determining unit 524 is also referred to as an "end control unit."

However, the embodiment is not limited to the case in which the determining unit 524 measures the number of times the count information is received from the PET scanner 200. For example, the determining unit 524 may measure the number of times the detector 210 detects radiation, on the basis of the count information stored in the count information table 511. For example, the determining unit 524 may classify the count information for each detection time with reference to the count information table 511, thereby measuring the number of times for one second. In addition, the embodiment is not limited to the case in which the determining unit 524 measures the number of times for every second, but the determining unit 524 may measure the number of times at any time interval. The embodiment is not limited to the case in which the determining unit 524 measures the number of times for the last one second, but the determining unit 524 may use any period of time.

The determining unit 524 determines whether the measured number of times is equal to or less than a threshold value. When it is determined that the measured number of times is equal to or less than the threshold value, the determining unit 524 controls the detector 210 to end the detection process. For example, a case in which "10" is set as the threshold value in advance will be described. In this case, whenever the number of times is measured, the determining unit 524 determines whether the measured number of times is less than "10." When it is determined that the measured number of times is not less than "10," the determining unit 524 does not perform any process. In this case, the process of the PET scanner 200 is continuously performed. On the other hand, when it is determined that the measured number of times is less than "10," the determining unit 524 ends the detection process of the PET scanner 200. In addition, the determining unit 524 repeats the determination process until the PET scanner 200 ends the detection process. An example of the flow of the process of the determining unit 524 will be described below. The determining unit 524 is also referred to as a "measuring unit" or an "end control unit."

An example of the flow of a PET image capture process of the PET-CT apparatus 100 according to the first embodiment will be described with reference to FIG. 9. FIG. 9 is a flowchart illustrating an example of the flow of the PET image capture process of the PET-CT apparatus according to the first embodiment. The PET-CT apparatus 100 captures an X-ray CT image before a series of processes, which will be described below.

As shown in FIG. 9, in the PET-CT apparatus 100, when an imaging request is received from the user (Yes in Step S101), the count information collecting unit 521 operates the PET scanner 200 such that the PET scanner 200 collects count information (Step S102). That is, whenever gamma rays are detected, the PET scanner 200 collects the detection position, the energy value, and the detection time.

Then, the count information collecting unit 521 stores the count information collected by the PET scanner 200 in the count information table 511 (Step S103). Then, the coincidence information generating unit 522 searches for a combination of count information items in which a difference in the detection time is within the time window width and the energy value is within the energy window width, with reference to the "detection time" and the "energy value" in the count information stored in the count information table 511 and generates coincidence information (Step S104).

Then, the PET image reconstruction unit 523 performs a back projection process using the coincidence information generated by the coincidence information generating unit 522 as projection data, thereby reconstructing a PET image (Step S105).

Figure 10:
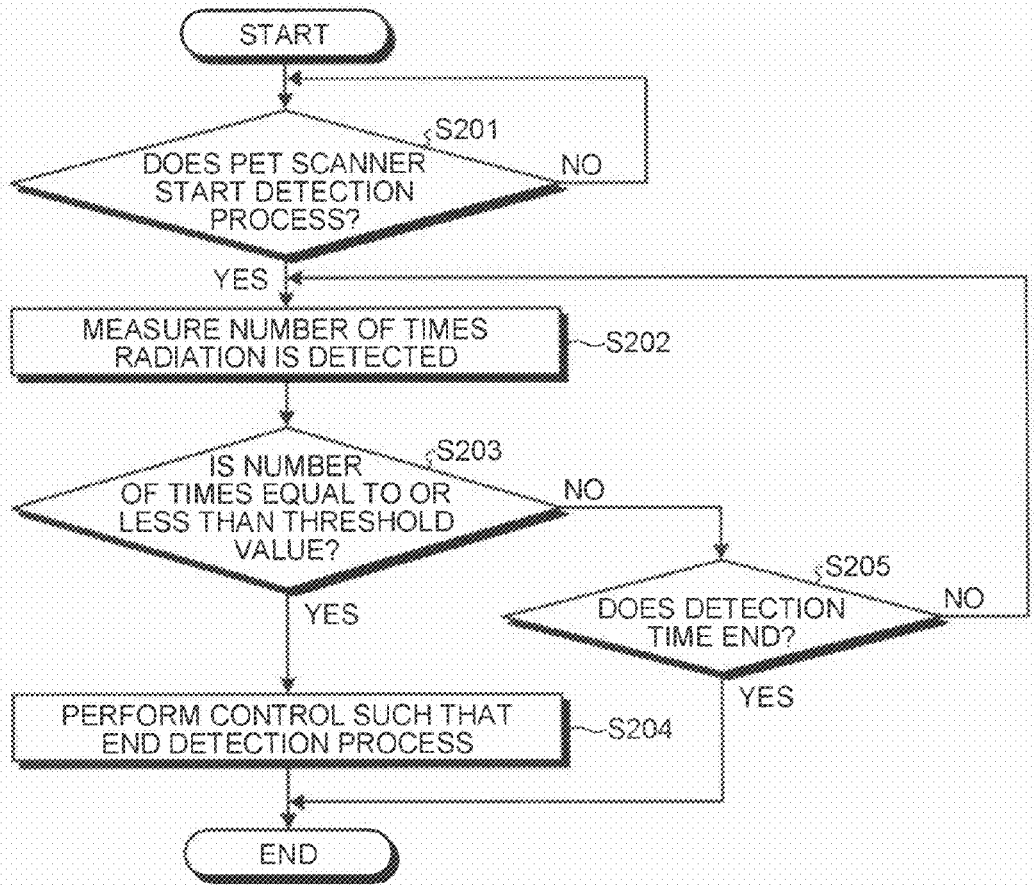
FIG. 10 is a diagram illustrating an example of the flow of the process of a determining unit according to the first embodiment.

Next, an example of the flow of the process of the determining unit according to the first embodiment will be described with reference to FIG. 10. FIG. 10 is a flowchart illustrating an example of the flow of the process of the determining unit according to the first embodiment. A series of processes, which will be described below, is repeatedly performed when the PET scanner 200 performs the detection process.

As shown in FIG. 10, when the PET scanner 200 starts the detection process (Yes in Step S201), the determining unit 524 measures the number of times the detector 210 detects radiation (Step S202). For example, the determining unit 524 measures the number of times the PET scanner 200 detects gamma rays for one second.

Then, the determining unit 524 determines whether the measured number of times is equal to or less than a threshold value (Step S203). For example, a case in which a threshold value "10" is set by the user in advance will be described. In this case, the determining unit 524 determines whether the number of times radiation is detected for one second is equal to or less than "10." When it is determined that the number of times radiation is detected for one second is equal to or less than the threshold value (Yes in Step S203), the determining unit 524 ends the detection process of the PET scanner 200 (Step S204).

On the other hand, when it is determined that the number of times radiation is detected for one second is more than the threshold value (No in Step S203), the determining unit 524 determines whether the detection time ends (Step S205). For example, when the time for which the detection process is performed is "30 minutes," the determining unit 524 determines whether "30 minutes" have elapsed from the start of the detection process of the PET scanner 200. When it is determined that the time has elapsed (Yes in Step S205), the determining unit 524 ends the process. On the other hand, when it is determined that the time has not elapsed (No in Step S205), the determining unit 524 returns to Step S202 and the process is repeatedly performed.

As described above, according to the first embodiment, the PET-CT apparatus 100 includes the detector 210 that detects radiation for generating a nuclear medicine image. In addition, the PET-CT apparatus 100 measures the number of times the detector 210 detects radiation. When the measured number of times is equal to or less than a threshold value, the PET-CT apparatus 100 controls the detector 210 to end the detection process. As a result, it is possible to prevent measurement from being continuously performed in a state in which radiation may not be detected.

Figure 11:
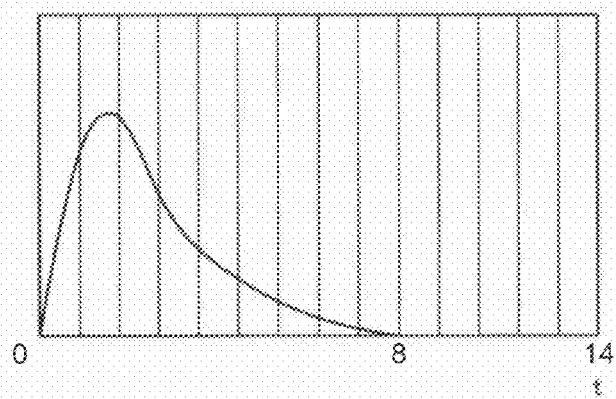
FIG. 11 is a diagram illustrating the effect of the PET-CT apparatus according to the first embodiment.

FIG. 11 is a diagram illustrating the effect of the PET-CT apparatus according to the first embodiment. In FIG. 11, the horizontal axis is a time axis and the vertical axis indicates the number of coincidence information items generated by the coincidence information generating unit 522. In the example shown in FIG. 11, the PET scanner 200 detects the detection time and the detection time is designated from "0" to "14" on the horizontal axis shown in FIG. 11.

For example, in a PET dynamic imaging operation that captures a plurality of PET images of the same part at different times, in many cases, an isotope or a labeled compound with a short half-life is used. As a result, before the PET-CT apparatus 100 ends the detection process, the dose of radiation detected by the detector 210 is attenuated and the coincidence information generating unit 522 may not generate the coincidence information. In the example shown in FIG. 11, at stage "8" on the horizontal axis, the coincidence information generated by the coincidence information generating unit 522 is "0." As a result, it is useless for the PET scanner 200 to continuously perform the detection process to stage "14." In contrast, the PET-CT apparatus 100 measures the number of times radiation is detected. When the measured number of times is equal to or less than a threshold value, the PET-CT apparatus 100 controls the detector 210 to end the detection process. Therefore, it is possible to prevent the PET dynamic operation from being continuously performed in a state in which the coincidence information may not be generated. In the example shown in FIG. 11, the PET-CT apparatus 100 can end the detection process at the stage "8" on the horizontal axis.

In the first embodiment, the determining unit 524 measures and determines the number of times the PET scanner 200 detects radiation. In a second embodiment, the determining unit 524 measures and determines the number of times the PET scanner 200 detects both a pair of radiations. In other words, in the second embodiment, determination is performed on the basis of the coincidence information. In the second embodiment, a description of the same points as those in the first embodiment will not be repeated, or the same points as those in the first embodiment will be described in brief.

Figure 12:
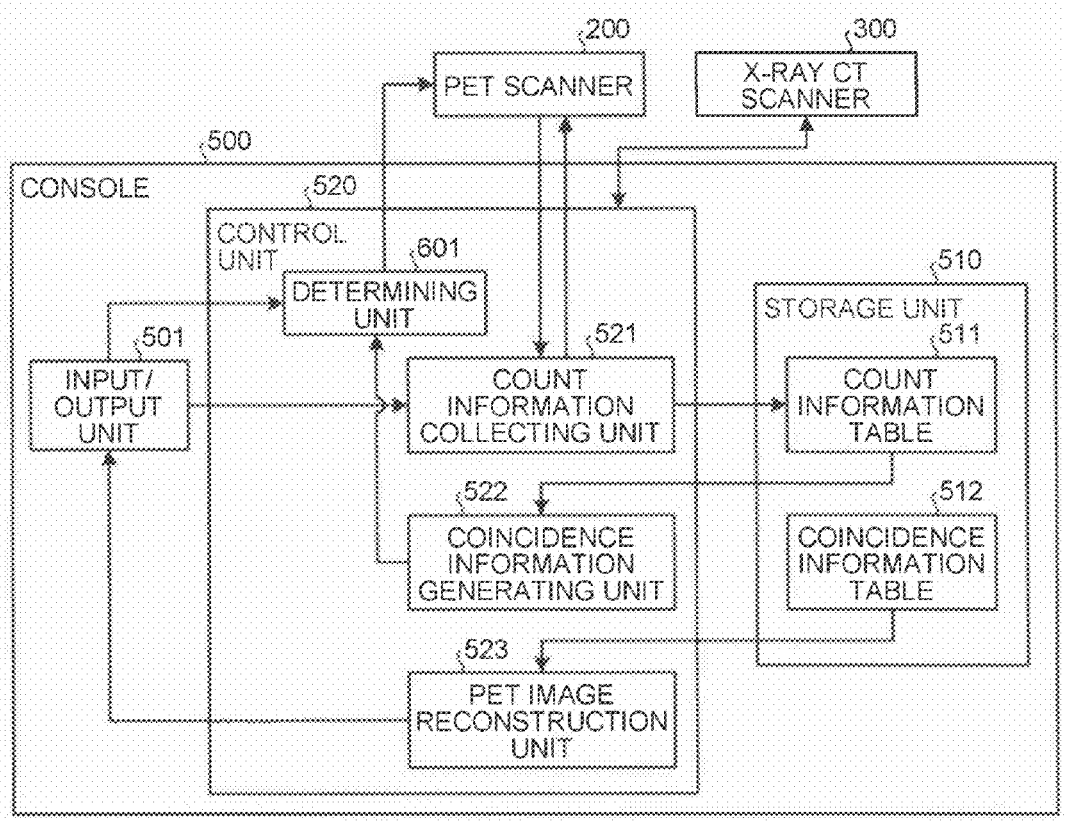
FIG. 12 is a block diagram illustrating an example of the structure of a console according to a second embodiment.

FIG. 12 is a block diagram illustrating an example of a console according to the second embodiment. In FIG. 12, the same blocks as those of the console 500 according to the first embodiment are denoted by the same reference numerals as those in FIG. 6 and a description thereof will not be repeated.

A determining unit 601 measures the number of times the detector 210 detects both a pair of radiations emitted from a positron emitting nuclide on the basis of the detection time and the detection position where the detector 210 detects the radiation. Specifically, the determining unit 601 measures the number of times the detector 210 detects both a pair of radiations on the basis of the coincidence information generated by the coincidence information generating unit 522. For example, the determining unit 601 classifies the coincidence information for each detection time with reference to the coincidence information table 512, thereby measuring the number of coincidence information items for every second. However, the embodiment is not limited thereto, but the number of coincidence information items may be measured by any method. For example, the determining unit 601 may generate the coincidence information separately from the process of the coincidence information generating unit 522 and measure the number of times on the basis of the generated coincidence information.

The determining unit 601 may measure the number of times the detector 210 detects a pair of radiations whose two detection positions are on a predetermined slice of interest, among the numbers of times the detector 210 detects a pair of radiations emitted from the positron emitting nuclide.

Figure 13:
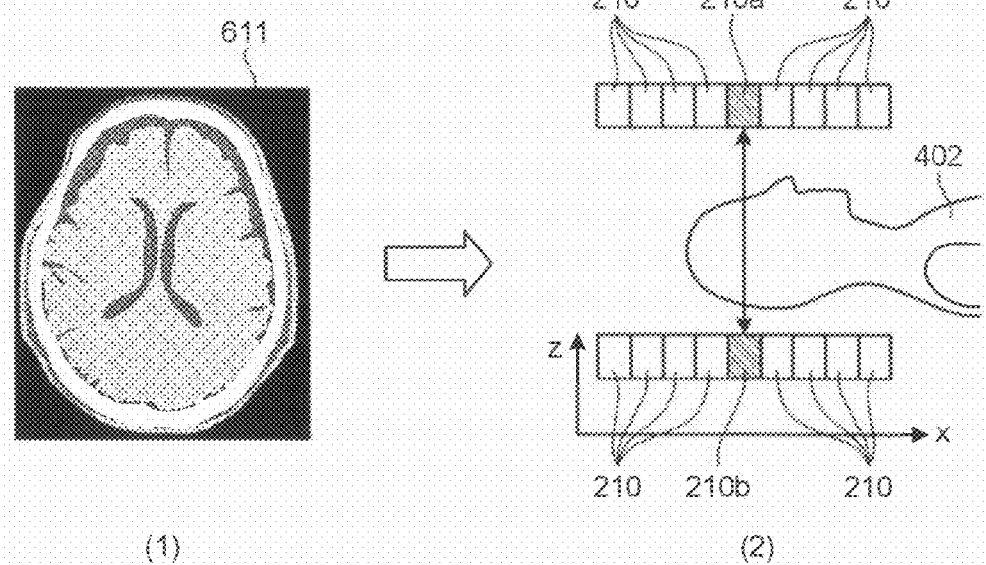
FIG. 13 is a diagram illustrating a pair of radiations in which two detection positions are on a predetermined slice of interest.

FIG. 13 is a diagram illustrating a pair of radiations whose two detection positions are on a predetermined slice of interest. (1) of FIG. 13 shows an example of the slice of interest. (2) of FIG. 13 shows the cross-sectional structure of the PET scanner 200. (2) of FIG. 13 also shows the examinee 402 for convenience of explanation. In FIG. 13, reference numeral 611 indicates the X-ray CT image of the slice of interest selected by the user, reference numeral 210 indicates a detector, and reference numerals 210a and 210b indicate the detectors 210 on the slice of interest. Reference numeral 402 indicates an examinee. As the X-ray CT image shown in (1) of FIG. 13, for example, an X-ray CT image captured before the PET image is used.

When the user selects a slice of interest as shown in (1) of FIG. 13, the determining unit 601 measures the number of coincidence information items in which the detector 210 disposed on the plane of the selected slice of interest is at the detection position, as shown in (2) of FIG. 13. For example, in the example shown in (2) of FIG. 13, the number of coincidence information items in which two detection positions are the detector 210a and the detector 210b is measured.

Specifically, when the user selects a slice of interest on the X-ray CT image 611, the determining unit 601 identifies the detector 210 that is disposed on the plane of the selected slice of interest. Then, the determining unit 601 measures the number of coincidence information items in which the detectors 210 identify both two detection positions among the coincidence information items generated by the coincidence information generating unit 522.

Figure 14:
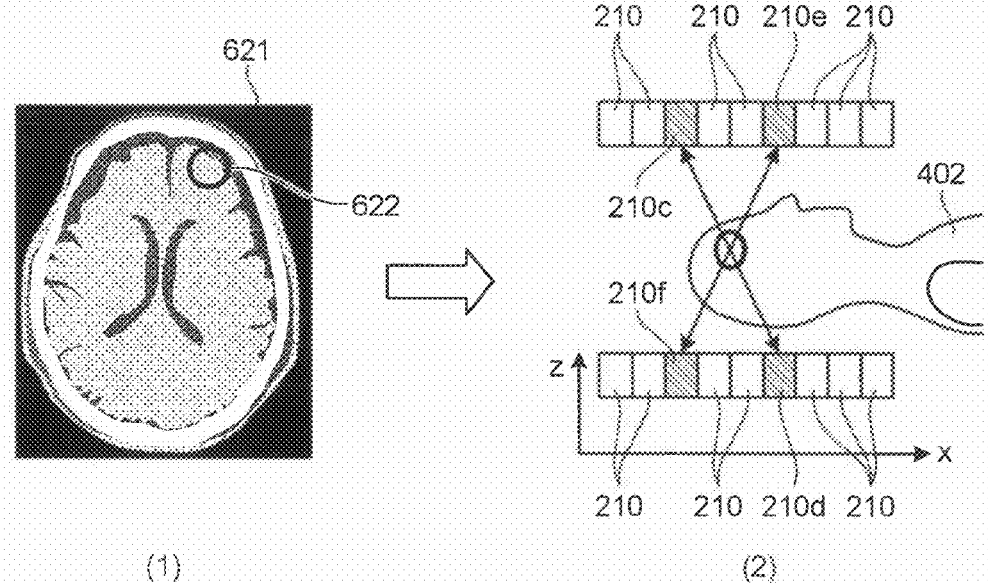
FIG. 14 is a diagram illustrating a pair of radiations on which a region of interest is disposed.

The determining unit 601 may measure the number of times the detector detects a pair of radiations having a region of interest on a line where gamma rays are emitted from the positron emitting nuclide. FIG. 14 is a diagram illustrating a pair of radiations on which the region of interest is disposed. (1) of FIG. 14 shows an example of the region of interest. (2) of FIG. 14 shows the cross-sectional structure of the PET scanner 200. (2) of FIG. 14 also shows the examinee 402 for convenience of explanation. In FIG. 14, reference numeral 621 indicates an X-ray CT image, reference numeral 622 indicates a region of interest, and reference numeral 210 indicates a detector. Reference numeral 402 indicates an examinee. FIG. 14 shows an example in which the region 622 of interest is on a line linking a detector 210c and a detector 210d and the region 622 of interest is on a line linking a detector 210e and a detector 210f. The region of interest is also referred to as an "ROI."

When the user selects the region 622 of interest as shown in (1) of FIG. 14, the determining unit 601 measures the number of times the detector 210 detects a pair of radiations on which the selected region 622 of interest is disposed, as shown in (2) of FIG. 14. For example, in the example shown in (2) of FIG. 14, the determining unit 601 measures the number of coincidence information items in which two detection positions are the detector 210c and the detector 210d and the number of coincidence information items in which two detection positions are the detector 210e and the detector 210f.

Specifically, when the user selects the region 622 of interest, the determining unit 601 identifies a combination of two detection positions where the region 622 of interest is disposed on the line. For example, in the example shown in (2) of FIG. 14, a combination of the detector 210c and the detector 210d and a combination of the detector 210e and the detector 210f are identified. Then, the determining unit 601 measures the number of coincidence information items, which is a combination of the detectors 210 identified by both two detection positions, among the coincidence information items generated by the coincidence information generating unit 522.

In this embodiment, the determining unit 601 identifies a combination of two detection positions where the region 622 of interest is disposed on the line in advance, but the embodiment is not limited thereto. Any other methods may be used.

As described above, according to the second embodiment, the PET-CT apparatus 100 measures the number of times the detector 210 detects both a pair of radiations. As a result, it is possible to continuously perform the PET dynamic imaging operation or stop the PET dynamic imaging operation on the basis of whether information used to reconstruct the PET image is obtained. That is, the coincidence information is used to reconstruct the PET image. In other words, when the detector 210 detects only one of a pair of radiations, it is difficult to specify the incident angle of gamma rays using only one of the pair of radiations and the one radiation is not used to reconstruct the PET image. Therefore, the number of times the detector 210 detects both a pair of radiations, not the number of times the detector 210 detects gamma rays, is used to continuously perform or stop the PET dynamic imaging operation on the basis of the information used to reconstruct the PET image.

As described above, according to the second embodiment, the PET-CT apparatus 100 measures the number of times the detector 210 detects a pair of radiations whose two detection positions are on a predetermined slice of interest. In this way, it is possible to perform determination on the basis of whether the coincidence information used to reconstruct a PET image on the slice of interest is equal to or less than a threshold value. That is, it is possible to continuously perform or stop the PET dynamic imaging operation on the basis of the information used to reconstruct the PET image on the slice of interest selected by the user is obtained.

As described above, according to the second embodiment, the PET-CT apparatus 100 measures the number of times the detector detects a pair of radiations on which the region of interest is disposed. Therefore, it is possible to perform determination on the basis of whether the coincidence information used to reconstruct a PET image in the region of interest is equal to or less than a threshold value. That is, it is possible to continuously perform or stop the PET dynamic imaging operation on the basis of the information used to reconstruct the PET image on the region of interest selected by the user is obtained.

The first and second embodiments have been described above, but the embodiment is not limited to the first and second embodiments. The embodiment may be applied to other embodiments, which will be described below.

For example, the control unit 520 may calculate the sum of the number of times radiation is detected and end the PET dynamic imaging operation when the sum of the number of times is more than a predetermined threshold value. In this case, the control unit 520 may measure the number of times the detector 210 detects both a pair of radiations, or the number of times the detector 210 detects a pair of radiations on which the region of interest is disposed.

For example, in the above-described embodiments, the console 500 receives the count information from the PET scanner 200 and uses it. However, the embodiment is not limited thereto. For example, the console 500 may receive the detection result of the detector 210 from the PET scanner 200. In this case, the console 500 receives waveform data output from the photomultiplier tube 213 and generates the count information from received waveform data.

For example, in the above-described embodiments, the console 500 receives the count information from the PET scanner 200 and generates the coincidence information. However, the embodiment is not limited thereto. For example, the PET scanner 200 may generate the coincidence information from the count information and transmit the generated coincidence information to the console 500. In this case, for example, the console 500 may receive, as information for determination, the count information or the waveform data output from the photomultiplier tube 213, separately from the coincidence information received from the PET scanner 200.

For example, in the above-described embodiments, the determining unit determines whether the number of times the detector 210 detects radiation is equal to or less than a threshold value. When it is determined that the number of times is equal to or less than the threshold value, the determining unit controls the detector 210 to end the detection process. However, the embodiment is not limited thereto. The determining unit may control the detector 210 to end the detection process when the differential value of the number of times the detector 210 detects radiation with respect to time is equal to or less than a predetermined value.

This will be described with reference to FIG. 11. As described above, in FIG. 11, the horizontal axis is a time axis and the vertical axis indicates the number of coincidence information items generated by the coincidence information generating unit 522. In the example shown in FIG. 11, the determining unit calculates the differential value of the measured number of times with respect to time at a predetermined timing. For example, the determining unit measures the gradient of a tangent line at "t=1" in FIG. 11 as a differential value at "t=1" in FIG. 11. Then, the determining unit determines whether the measured value is equal to or less than a predetermined value. When it is determined that the measured value is equal to or less than the predetermined value, the determining unit controls the detector 210 to end the detection process.

As shown in FIG. 11, the differential value of the number of times radiation is measured with respect to time is a positive value from "t=0" to the peak which is in the vicinity of "t=2" and is a negative value after the peak that is in the vicinity of "t=2." As a result, the use of the differential value makes it possible to simply determine whether the number of times radiation is measured tends to increase or decrease and then end the measurement on the basis of the determination result.

The determining unit uses a gradient corresponding to the threshold value according to the first embodiment as the predetermined value. The determining unit may use any value as the predetermined value. For example, the determining unit may use "0" as the predetermined value. In other words, the determining unit may control the detector 210 to end the detection process when the differential value is "0."

Next, a supplementary description of the case in which "0" is used as the predetermined value will be made. That is, a case in which the detection process ends when the detector 210 does not detect radiation will be described. As shown in FIG. 11, the differential value of the number of times radiation is measured with respect to time is "0" once at the peak that is in the vicinity of "t=2" and is also "0" in the vicinity of "t=8" where radiation is not detected. On the basis of this point, when "0" is used as the predetermined value, the determining unit determines whether the differential value becomes a negative value and then becomes "0," or determines whether the differential value becomes "0" once and then becomes "0" again.

The determining unit may use any timing as the predetermined timing. For example, the determining unit may periodically perform the measurement. Specifically, the determining unit may perform the measurement at an interval of one second or two seconds.

For example, the determining unit may perform determination on the basis of whether the differential value of the number of coincidence information items generated by the coincidence information generating unit 522 with respect to time is equal to or less than a predetermined value or whether the sum of the number of times radiation is detected is equal to or less than a predetermined value.

Among the processes in the above-mentioned embodiments, some or all of the processes that are automatically performed may be manually performed, or some or all of the processes that are manually performed may be automatically performed by a known method. In addition, information including the process sequence, the control sequence, the detailed names, and various kinds of data or parameters described in the specification or the drawings (FIGS. 1 to 14) may be arbitrarily changed except for special cases.

The drawings show the function and concept of the components of each apparatus, but the components of each apparatus are not necessarily physically configured as shown in the drawings. That is, the examples of the separation or integration of the apparatuses are not limited to those shown in the drawings, but some or all of the apparatuses may be functionally or physically separated or integrated in any unit according to various kinds of loads or use conditions. For example, in the above-described embodiments, the console 500 reconstructs the PET image or the X-ray CT image and performs determination on the basis of the number of time radiation is detected. However, the embodiment is not limited thereto. For example, the control unit that performs determination on the basis of the number of time radiation is detected may be provided separately from the console 500. In this case, the control unit that performs determination on the basis of the number of time radiation is detected may be provided outside the PET-CT apparatus 100 and may be connected to the PET-CT apparatus 100 through a network.

A control program of the nuclear medicine imaging apparatus according to the above-described embodiments may be distributed through a network, such as the Internet. In addition, the control program may be stored in a computer-readable recording medium, such as a hard disk, a flexible disk (FD), a CD-ROM, an MO, or a DVD, may be read from the recording medium by a computer, and may be executed.

While certain embodiments have been described, these embodiments have been presented by way of example only, and are not intended to limit the scope of the embodiments. Indeed, the novel apparatuses, methods, and products described herein may be embodied in a variety of other forms; furthermore, various omissions, substitutions and changes in the form of the apparatuses, methods, and products described herein may be made without departing from the spirit of the embodiments. The accompanying claims and their equivalents are intended to cover such forms or modifications as would fall within the scope and spirits of the embodiments.

According to nuclear medicine imaging apparatus of at least one embodiment described above, the nuclear medicine imaging apparatus includes a detector that detects radiation for generating a nuclear medicine image; a measuring unit that measures the number of times the detector detects the radiation; and an end control unit that controls the detector to end the detection operation. As a result, it is possible to prevent measurement from being continuously performed in a state in which radiation is not detected.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A nuclear medicine imaging apparatus comprising:
   a detector configured to detect radiation for generating a nuclear medicine image;
   a measuring unit configured to measure the number of times the detector detects the radiation; and
   an end control unit configured to control the detector to end the detection operation when the number of times measured by the measuring unit is equal to or less than a threshold value.

2. The nuclear medicine imaging apparatus according to claim 1, further comprising:
   an acquiring unit configured to acquire a detection position where the detector detects the radiation and a detection time when the detector detects the radiation,
   wherein the measuring unit is configured to measure the number of times the detector detects both a pair of radiations emitted from a positron emitting nuclide, on the basis of the detection position and the detection time acquired by the acquiring unit.

3. The nuclear medicine imaging apparatus according to claim 2,
   wherein the measuring unit is configured to measure the number of times the detector detects the pair of radiations whose two detection positions are on a predetermined slice of interest.

4. The nuclear medicine imaging apparatus according to claim 2,
   wherein the measuring unit is configured to measure the number of times the detector detects the pair of radiations having a region of interest on a line where the radiations are emitted from the positron emitting nuclide.

5. A control method comprising:
   detecting radiation for generating a nuclear medicine image;
   measuring the number of times the radiation is detected; and
   ending the detection operation when the measured number of times is equal to or less than a threshold value.

6. A non-transitory computer readable medium comprising instructions that cause a computer to execute:
   detecting radiation for generating a nuclear medicine image;
   measuring the number of times the radiation is detected; and
   ending the detection operation when the measured number of times is equal to or less than a threshold value.

7. A nuclear medicine imaging apparatus comprising:
   a detector configured to detect radiation for generating a nuclear medicine image;

a measuring unit configured to measure the number of times the detector detects the radiation; and an end control unit configured to control the detector to end the detection operation when a differential value of the number of times measured by the measuring unit with respect to time is equal to or less than a predetermined value.

8. The nuclear medicine imaging apparatus according to claim 7, wherein the end control unit is configured to control the detector to end the detection operation when the differential value is 0.

9. A control method comprising:

detecting radiation for generating a nuclear medicine image;

measuring the number of times the radiation is detected; and ending the detection operation when a differential value of the measured number of times with respect to time is equal to or less than a predetermined value.

10. A non-transitory computer readable medium comprising instructions that cause a computer to execute:

detecting radiation for generating a nuclear medicine image;

measuring the number of times the radiation is detected; and ending the detection operation when a differential value of the measured number of times with respect to time is equal to or less than a predetermined value.

* * * * *